(12) United States Patent
Garner et al.

(10) Patent No.: US 6,171,996 B1
(45) Date of Patent: Jan. 9, 2001

(54) HYDROCYANATION PROCESSES AND MULTIDENTATE PHOSPHITE LIGAND AND NICKEL CATALYST COMPOSITIONS THEREFOR

(75) Inventors: James Michael Garner; Kristina Ann Kruetzer, both of Wilmington, DE (US); Wilson Tam, Boothwyn, PA (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/351,642

(22) Filed: Jul. 13, 1999

Related U.S. Application Data

(62) Division of application No. 09/121,105, filed on Jul. 23, 1998
(60) Provisional application No. 60/053,831, filed on Jul. 29, 1997.

(51) Int. Cl.[7] ............ C07C 253/00; B01J 31/00
(52) U.S. Cl. ............ 502/162; 558/338
(58) Field of Search ............ 558/338; 502/162

(56) References Cited

U.S. PATENT DOCUMENTS

| | | | |
|---|---|---|---|
| 3,496,215 | 2/1970 | Drinkard et al. | 260/465.8 |
| 3,496,217 | 2/1970 | Drinkard, Jr. et al. | 260/465.8 |
| 3,496,218 | 2/1970 | Drinkard, Jr. | 260/465.8 |
| 3,631,191 | 12/1971 | Kane et al. | 260/439 R |
| 3,655,723 | 4/1972 | Drinkard, Jr. | 260/465.3 |
| 3,766,237 | 10/1973 | Chia et al. | 260/465.3 |
| 4,774,353 | 9/1988 | Hall et al. | 558/335 |
| 4,874,884 | 10/1989 | McKinney et al. | 558/338 |
| 5,512,696 | 4/1996 | Kreutzer et al. | 558/338 |
| 5,910,600 | 6/1999 | Urata et al. | 558/162 |

FOREIGN PATENT DOCUMENTS

| | | | |
|---|---|---|---|
| WO 93/03839 | 3/1993 | (WO) | B01J/31/24 |
| WO 95/28228 | 10/1995 | (WO) | B01J/31/18 |
| WO 96/11182 | 4/1996 | (WO) | C07C/253/10 |

OTHER PUBLICATIONS

Tolman et al., *Advances in Catalysis*, 33, No. 1, 1985.
M.J. Baker et al., *J. Chem. Soc., Chem. Commun.*, 1292, 1991.
Baker et al., *J. Chem. Soc., Chem. Commun.*, 803, 1991.
Cuny et al., *J. Am. Chem. Soc.*, 115, 2066, 1993.

*Primary Examiner*—Cecilia Tsang
*Assistant Examiner*—Joseph Murray

(57) ABSTRACT

A process for hydrocyanation of an aliphatic monoethylenically unsaturated compound, in which the ethylenic double bond is not conjugated to any other unsaturated group in the molecule, or a monoethylenically unsaturated compound in which the ethylenic double bond is conjugated to an ester group, which process uses a catalyst composition comprising a zero-valent nickel and a multidentate phosphite ligand in the presence of a Lewis acid promoter.

5 Claims, No Drawings

HYDROCYANATION PROCESSES AND MULTIDENTATE PHOSPHITE LIGAND AND NICKEL CATALYST COMPOSITIONS THEREFOR

This Application claims benefit to Provisional Application Ser. No. 60/053,831 filed Jul. 29, 1997.

This is a division of application Ser. No. 09/121,105 filled Jul. 23, 1998, now allowed May 24, 2000.

FIELD OF THE INVENTION

The invention generally relates to a process and catalyst precursor composition for the hydrocyanation of monoethylenically unsaturated compounds wherein zero-valent nickel and a multidentate phosphite ligand are used in the presence of a Lewis acid promoter.

BACKGROUND OF THE INVENTION

Hydrocyanation catalyst systems, particularly pertaining to the hydrocyanation of ethylenically unsaturated compounds, are known in the art. For example, systems useful for the hydrocyanation of butadiene to form pentenenitrile (PN) and in the subsequent hydrocyanation of pentenenitrile to form adiponitrile (ADN), are known in the commercially important nylon synthesis field.

The hydrocyanation of ethylenically unsaturated compounds using transition metal complexes with monodentate phosphite ligands is documented in the prior art. See, for example, U.S. Pat. Nos. 3,496,215; 3,631,191; 3,655,723; and 3,766,237, and Tolman et al., Advances in Catalysis, 1985, 33, 1. The hydrocyanation of activated ethylenically unsaturated compounds, such as with conjugated ethylenically unsaturated compounds (e.g., butadiene and styrene), and strained ethylenically unsaturated compounds (e.g., norbomene) proceeds without the use of a Lewis acid promoter, while hydrocyanation of unactivated ethylenically unsaturated compounds, such as 1-octene and 3-pentenenitrile, requires the use of a Lewis acid promoter.

Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. Moreover, U.S. Pat. No. 4,874,884 discloses a process for producing ADN by the zero-valent nickel-catalyzed hydrocyanation of pentenenitriles in the presence of a synergistic combination of promoters selected in accordance with the reaction kinetics of the ADN synthesis.

Phosphite ligands have been shown to be useful ligands in the hydrocyanation of activated ethylenically unsaturated compounds. See, for example, Baker, M. J., and Pringle, P. G., *J Chem. Soc. Chem. Commun.,* 1991, 1292; Baker et al., *J Chem. Soc., Chem. Commun.,* 1991, 803; Union Carbide, WO 93,03839. Also, phosphite ligands have been disclosed with rhodium in the hydroformylation of functionalized ethylenically unsaturated compounds: see, Cuny et al., *J. Am. Chem. Soc.,* 1993, 115, 2066.

U.S. Pat. No. 5,512,696, which issued Apr. 30, 1996, discloses processes and catalyst compositions for the hydrocyanation of monoethyleneically unsaturated compounds using zero-valent nickel and certain multidentate phosphite ligands, and Lewis acid promoters, which are similar to those encompassed by the present invention, except for the choice of the ortho substituent for the group or the phosphite phenyl termin.

Like U.S. Pat. No. 5,512,696, the present invention provides processes and catalyst precursor compositions which are more rapid, selective, efficient and stable than prior processes and catalyst complexes employed in the hydrocyanation of monoethylenically unsaturated compounds. Other objects and advantages of the present invention will become apparent to those skilled in the art upon reference to the detailed description of the invention which hereinafter follows.

SUMMARY OF THE INVENTION

The present invention provides for a hydrocyanation process, comprising reacting an acyclic, aliphatic, monoethylenically unsaturated compound in which the ethylenic double bond is not conjugated to any other olefinic group in the molecule, or a monoethylenically unsaturated compound in which the ethylenic double bond is conjugated to an organic ester group, with a source of HCN in the presence of a catalyst precursor composition comprising a Lewis acid, a zero-valent nickel, and at least one multidentate phosphite ligand selected from the group represented by the following Formulas I, II, III, IV, V, VI, VII, VIII, and IX, in which all like reference characters have the same meaning, except as further explicitly limited.

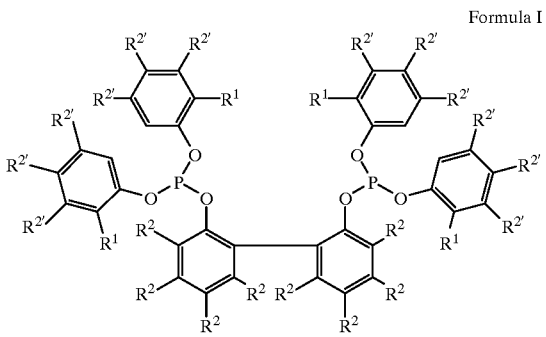

Formula I

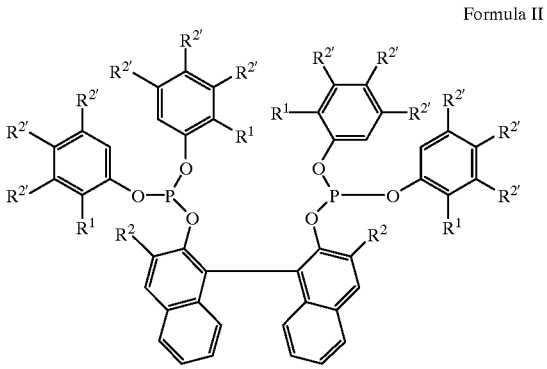

Formula II

Formula III
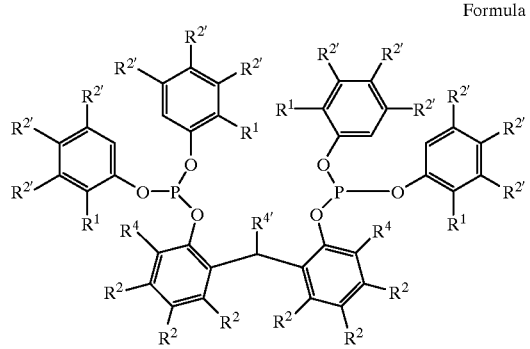

Formula VII
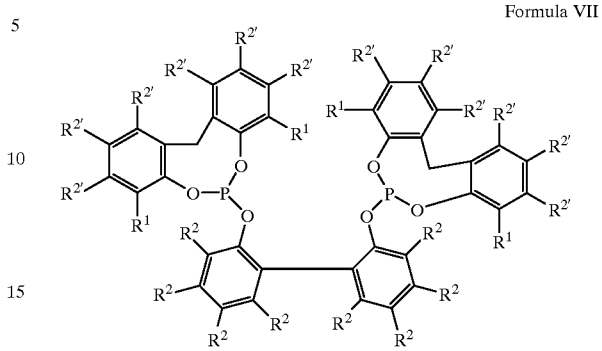

Formula IV
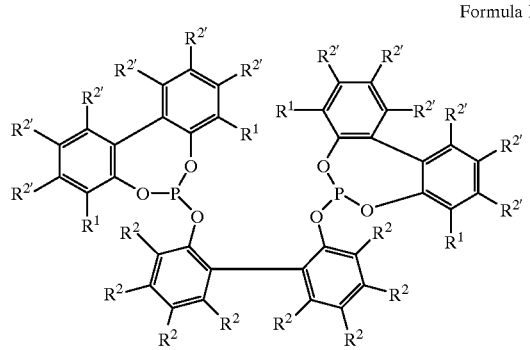

Formula VIII
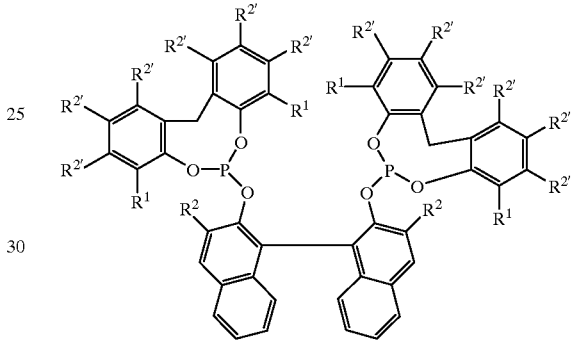

Formula V
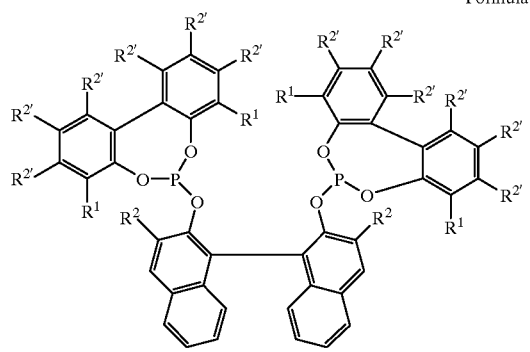

Formula IX
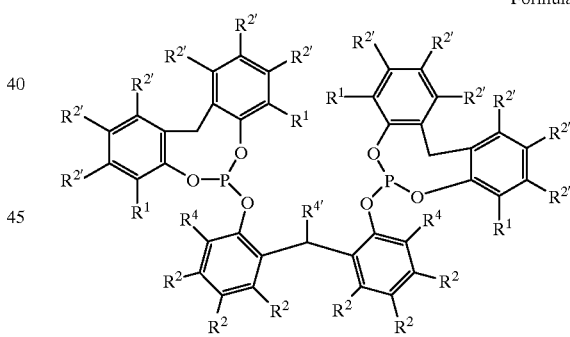

Formula VI
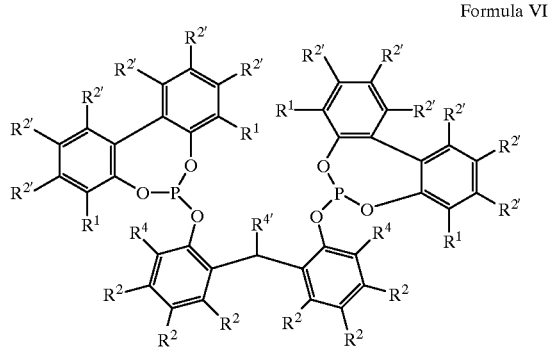

wherein each $R^1$ is independently a primary, secondary, or tertiary hydrocarbyl of 1 to 12 carbon atoms; with the proviso that at least one of $R^1$ must be a primary hydrocarbyl;

each $R^2$ is independently H, halogen, primary or secondary hydrocarbyl of 1 to 12 carbon atoms, $OR^3$ wherein $R^3$ is a $C_1$ to $C_{12}$ alkyl, or $CO_2R^{3'}$ wherein $R^{3'}$ is an aryl or a $C_1$ to $C_{12}$ alkyl;

each $R^{2'}$ is independently H, halogen, CHO, primary, secondary or tertiary hydrocarbyl of 1 to 12 carbon atoms, $OR^3$ wherein $R^3$ is a $C_1$ to $C_{12}$ alkyl, $CO_2R^{3'}$ wherein $R^{3'}$ is an aryl or a $C_1$ to $C_{12}$ alkyl, or $C(R^3)(O)$ wherein $R^3$ is a $C_1$ to $C_{12}$ alkyl;

each $R^4$ is independently H, a primary or secondary hydrocarbyl of 1 to 12 carbon atoms or $CO_2R^3$ wherein $R^3$ is a $C_1$ to $C_{12}$ alkyl; and each $R^{4'}$ is independently H, a primary or secondary hydrocarbyl of 1 to 12 carbon atoms or aryl.

In the above catalyst precursor compositions, the Lewis acid is considered to be a promoter.

The term "hydrocarbyl" is well known in the art and designates a hydrocarbon molecule from which one hydrogen atom has been removed. Such molecules can contain single, double or triple bonds.

The present invention further provides for novel multidentate phosphite ligands selected from one of Formulas I–IX, as defined above and catalyst precursor compositions made therefrom with zero-valent nickel. Preferably, the catalyst precursor compositions also have a Lewis acid present.

DETAILED DESCRIPTION OF THE PREFERRED EMBODIMENTS

Representative ethylenically unsaturated compounds which are useful in the process of this invention are shown in Formulas X or XII, and the corresponding terminal nitrile compounds produced are illustrated by Formulas XI or XII, respectively, wherein like reference characters have same meaning.

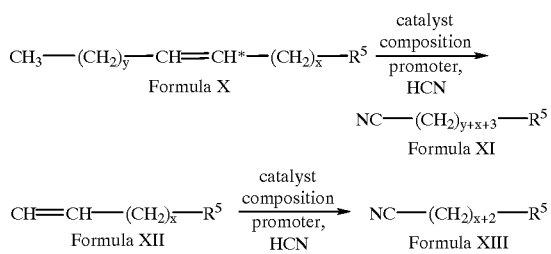

wherein $R^5$ is H, CN, $CO_2R^{3'}$, or perfluoroalkyl;

y is an integer of 0 to 12;

x is an integer of 0 to 12 when $R^5$ is H, $CO_2R^{3'}$ or perfluoroalkyl;

x is an integer of 1 to 12 when $R^5$ is CN; and $R^{3'}$ is aryl or a $C_1$ to $C_{12}$ alkyl.

One of the ligands useful in the catalyst compositions of the present invention is illustrated above by Formula I, as defined above. At least one of $R^1$ is a primary alkyl, examples of which include methyl, ethyl and n-propyl. In the preferred Formula I ligand, each $R^1$ is methyl, each $R^2$ is methyl except $R^2$ para to oxygen. $R^2$ para to oxygen is hydrogen and $R^{2'}$ is hydrogen.

The catalyst composition of the invention may be considered a "precursor" composition in that the zero-valent nickel at some point becomes complexed to the multidentate phosphite ligand, and, further in all likelihood, additional reactions occur during hydrocyanation, such as, for example, complexing of the initial catalyst composition to an ethylenically unsaturated compound.

These ligands can be prepared by a variety of methods known in the art, for example, see descriptions in European Patent Application 92109599.8 of Mitsubishi Kasei Corporation and the corresponding U.S. Pat. No. 5,235,113 to Sato et al. The reaction of o-cresol with phosphorus trichloride gives the phosphorochloridite. The reaction of this phosphorochloridite with 3,3',4,4',6,6'-hexamethyl-2,2'-biphenol in the presence of triethylamine gives the above-identified preferred ligand of Formula I.

The phosphorochloridite may be prepared by a variety of methods known in the art, for example, see descriptions in *Polymer,* 1992, 33, 161; *Inorganic Synthesis,* 1966, 8, 68;.U.S. Pat. No. 5,210,260; *Z. Anorg. Allg. Chem.,* 1986, 535, 221. With bulky ortho-substituted phenols (e.g., 2-t-butylphenol), phosphorochloridites can be prepared in situ from $PCl_3$ and the phenol. With less bulky groups, purification by high vacuum distillation is typically necessary. High vacuum distillation is difficult for large scale operations. An improved process for preparing the phosphochlorodite comprises treatment of N,N-dialkyl diarylphosphoramidite with HCl. $ClP(OMe)_2$ has been prepared in this manner, see *Z. Naturforsch,* 1972, 27B, 1429. Phosphorochloridites derived from substituted phenols have been prepared using this procedure as described in copending commonly assigned application Ser. No. 08/563,718, filed Nov. 28, 1995. It has also been found that phosphorochloridite of o-cresol can be prepared in situ from $PCl_3$ and o-cresol.

The zero-valent nickel compounds can be prepared or generated according to techniques well known in the art, as described, for example, in U.S. Pat. Nos. 3,496,217; 3,631,191; 3,846,461; 3,847,959; and 3,903,120, which are incorporated herein by reference. Zero-valent nickel compounds that contain ligands which can be displaced by the organophosphorus ligand are a preferred source of zero-valent nickel. Two such preferred zero-valent nickel compounds are $Ni(COD)_2$ (COD is 1,5-cyclooctadiene) and $Ni\{P(O-o-C_6H_4CH_3)_3\}_2(C_2H_4)$, both of which are known in the art. Alternatively, divalent nickel compounds may be combined with a reducing agent, to serve as a source of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated cataylst, as described in U.S. Pat. No. 3,903,120, is also a suitable source of zero-valent nickel.

The nonconjugated acyclic, aliphatic, monoethylenically unsaturated starting materials useful in this invention include unsaturated organic compounds containing from 2 to approximately 30 carbon atoms. 3-Pentenenitrile and 4-pentenenitrile are especially preferred. As a practical matter, when the nonconjugated acyclic aliphatic monoethylenically unsaturated compounds are used in accordance with this invention, up to about 10% by weight of the mono-ethylenically unsaturated compound may be present in the form of a conjugated isomer, which itself may undergo hydrocyanation. For example, when 3-pentene-nitrile is used, as much as 10% by weight thereof may be 2-pentenenitrile. (As used herein, the term "pentenenitrile" is intended to be identical with "cyanobutene"). Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc., nonconjugated diethylenically unsaturated compounds such as allene, substituted compounds such as 3-pentenenitrile, 4-pentenenitrile, methyl pent-3-enoate, and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

The starting ethylenically unsaturated compounds useful in this invention and the hydrocyanation products thereof are those shown above in Formulas X through XII. Those of Formula X yield terminal nitrites of Formula XI, while those of Formula XII yield terminal nitriles of Formula XIII.

Preferred are nonconjugated linear alkenes, nonconjugated linear alkene-nitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH=CH_2$ (where z is 1 to 12).

The preferred products are terminal alkanenitriles, linear dicyanoalkylenes, linear aliphatic cyanoesters, and 3-(perfluoroalkyl)propionitrile. Most preferred products are adiponitrile, alkyl 5-cyanovalerate and $C_zF_{2z+1}CH_2CH_2CN$, where z is 1 to 12.

The present hydrocyanation process may be carried out, for example, by charging a reactor with the reactants, catalyst composition, and solvent, if any; but preferably, the hydrogen cyanide is added slowly to the mixture of the other components of the reaction. Hydrogen cyanide may be delivered as a liquid or as a vapor to the reaction. Another suitable technique is to charge the reactor with the catalyst and the solvent to be used, and feed both the unsaturated compound and the HCN slowly to the reaction mixture. The molar ratio of unsaturated compound to catalyst can be varied from about 10:1 to about 2000:1.

Preferably, the reaction medium is agitated, for example, by stirring or shaking. The reaction product can be recovered by conventional techniques such as, for example, by distillation. The reaction may be run either batchwise or in a continuous manner.

The hydrocyanation reaction can be carried out with or without a solvent. The solvent, if used, should be liquid at the reaction temperature and pressure and inert towards the unsaturated compound and the catalyst. Suitable solvents include hydrocarbons, such as benzene or xylene, and nitriles, such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from −25° C. to 200° C. can be used, the range of 0° C. to 150° C. being preferred.

Atmospheric pressure is satisfactory for carrying out the present invention and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

One embodiment of the invention is a catalyst precursor composition comprising zero valent nickel and a multidentate phosphite ligand select from the group represented by the following Formula I, II, III, IV, V, VI, VII, VIII and IX, as described above, wherein the zero-valent nickel and the multidentate phosphite ligand are supported on the same solid support.

EXAMPLES

The following non-limiting, representative examples illustrate the process and catalyst compositions of this invention. All parts, proportions, and percentages are by weight, unless otherwise indicated. In each example, the following procedure was used unless otherwise noted.

The mixtures were heated in a thermostatically-controlled oil bath. HCN was delivered to the flask as an $HCN/N_2$ gas mixture by bubbling dry nitrogen carrier gas through liquid HCN maintained in an ice bath at 0° C. This provided a vapor stream which was about 35% HCN (vol/vol). Samples were periodically analyzed by gas chromatography (GC). In the examples, ADN stands for adiponitrile, MGN stands for 2-methylglutaronitrile, and ESN stands for ethylsuccinonitrile. COD stands for 1,5-cyclooctadiene and THF stands for tetrahydrofuran.

EXAMPLE 1

Synthesis of the ligand of Formula II where $R^1$ is n-propyl, $R^2$ and $R^{2'}$ are Hydrogen

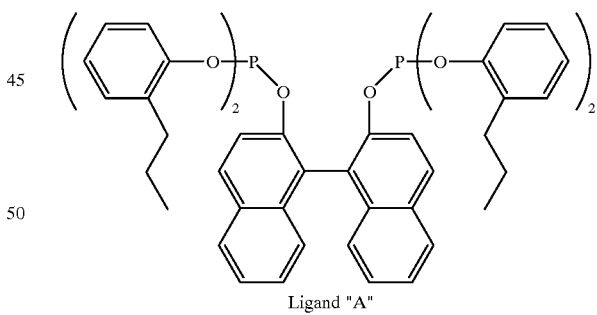

Ligand "A"

To a 200 mL round bottom flask, 1.09 g 2-n-propylphenol (8 mmol) and 0.55 g $PCl_3$ (4 mmol) were added, followed by the addition of 80 mL dry toluene. The flask was cooled to −30° C. and a precooled toluene solution (−30° C., 20 mL) containing 1.0 g $NEt_3$ (10 mmol) was added dropwise. About 1 hour later, the $^{31}P$ NMR spectrum of the reaction mixture in toluene/$C_6D_6$ showed a single peak at 162.30 ppm. A toluene solution (20 mL) containing 0.57 g 1,1'-binaphthol (4 mmol) and 0.4 g $NEt_3$ (4 mmol) was added to the above solution and stirred for 0.5 hour. The mixture was filtered through Celite® (a product of Johns-Manville Company) washed with 10 mL toluene and the solvent was taken off under vacuum. The product was dried under vacuum overnight. $^1$H NMR (300.15 MHz, $C_6D_6$): δ 0.76 (t, 12 H), 1.43 (m, 8 H), 2.41 (m, 8 H), 6.7~7.7 (m, 28 H), $^{31}$P NMR (121.77 MHz, $C_6D_6$):130.63 ppm. FB MS (Fast Atom Bombardment Mass Spectroscopy) m/z:(M+1) measured: 885.24; calcd mass: 885.35.

EXAMPLE 1A

Hydrocyanation of 3-Pentenenitrile with Ligand "A"/Ni $(COD)_2$; $ZnCl_2$ promoter 325 mg of Ligand "A", 40 mg Ni$(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 68.2% ADN, 9.1% MGN, and 1.4% ESN (selectivity to ADN: 86.6%).

EXAMPLE 2

Synthesis of the ligand of Formula II where each $R^1$ is ethyl, $R^2$ and $R^{2'}$ are Hydrogen

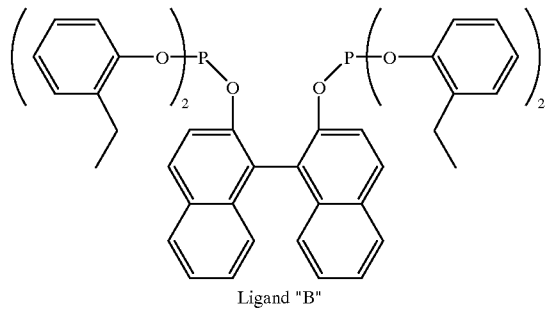

Ligand "B"

The procedure was the same as in Example 1 but with 2-ethylphenol (978 mg, 8 mmoles), $PCl_3$ (549 mg, 4 mmoles) and $NEt_3$ (1 g, 10 mmoles) followed by, 1'-binaphthol (573 mg, 2 mmoles) and $NEt_3$ (0.5 g, 5 mmoles). $^{31}$P NMR(δ, $C_6D_6$): 130.94 ppm with minor peaks at 146.06 and 131.54 ppm.

EXAMPLE 2A

Hydrocyanation of 3-Pentenenitrile with Ligand "B"/Ni $(COD)_2$; $ZnCl_2$ promoter 348 mg of Ligand "B", 40 mg Ni$(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 73.5% ADN, 11.3% MGN, and 1.7% ESN (selectivity to ADN: 85.0%).

EXAMPLE 3

Synthesis of the ligand of Formula II where each $R^1$ is methyl, $R^2$ and $R^{2'}$ are Hydrogen

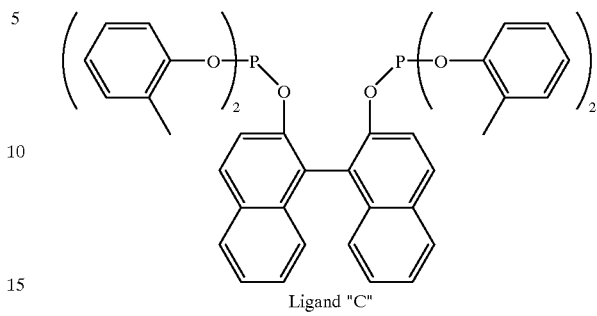

Ligand "C"

The procedure was the same as Example 1 but with o-cresol (865 mg, 8 mmoles), $PCl_3$ (550 mg, 4 mmoles) and $NEt_3$ (1 g, 10 mmoles) followed by 1,1'-binaphthol (573 mg, 2 mmoles) and $NEt_3$ (0.4 g, 4 mmoles). $^{31}$P NMR (δ, $C_6D6$): 130.65 ppm with minor peak at 131.37 ppm.

EXAMPLE 3A

Hydrocyanation of 3-Pentenenitrile with Ligand "C"/Ni $(COD)_2$; $ZnCl_2$ promoter 372 mg of Ligand "C", 40 mg Ni$(COD)_2$, and 20 mg of $ZnCl_2$ were dissolved in 5 mL of 3-pentenenitrile. The mixture was treated with HCN at a nitrogen flow rate of 30 ML/min at 70° C. for one hour. GC analysis indicated 79.5% ADN, 13.0% MGN, and 2.2% ESN (selectivity to ADN: 83.9%).

EXAMPLE 4

Synthesis of the ligand of Formula I where each $R^1$ is methyl, $R^{2'}$ is Hydrogen, each $R^2$ ortho to the oxygen is OMe and each $R^2$ para to the oxygen is methyl

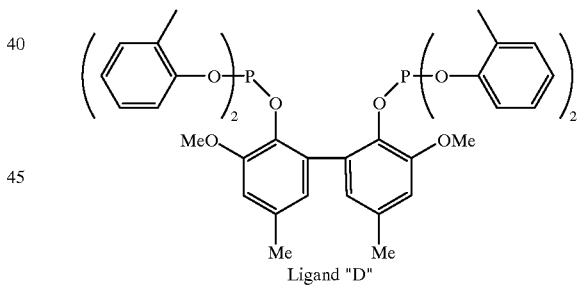

Ligand "D"

The procedure is the same as Example 1 but with o-cresol (865 mg, 8 mmoles), $PCl_3$ (550 mg, 4 mmoles) and $NEt_3$ (1 g, 10 mmoles) followed by 2,2'-dihydroxy-3,3'-dimethoxy-5,5'-dimethyl-1,1'-biphenylene (550 mg, 2 mmoles) and $NEt_3$ (0.4 g, 4 mmoles). The 2,2'-dihydroxy-3,3'-dimethoxy-5,5'-dimethyl-1,1'-biphenylene was prepared by coupling 2-methoxy-4-methylphenol using the procedure described in *Phytochemistry*, 1988, 27, 3008. $^{31}$P NMR ($C_6D_6$): 133.68 ppm with minor peaks at 144.9, 136.9, 134.3, and 131.5 ppm.

EXAMPLE 4A

Hydrocyanation of 3-Pentenenitrile with Ligand "D"/Ni $(COD)_2$; $ZnCl_2$ promoter 320 mg of Ligand "D", 40 mg Ni$(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 81.4% ADN, 5.9% MGN, and 0.6% ESN (selectivity to ADN: 92.6%).

EXAMPLE 5

Synthesis of the ligand of Formula I where each $R^1$ is methyl and each $R^2$ and $R^{2'}$ is Hydrogen

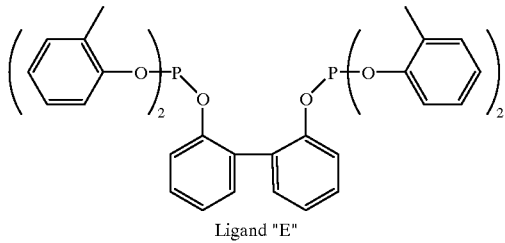

Ligand "E"

The procedure is the same as Example 1 but with o-cresol (865 mg, 8 mmoles), $PCl_3$ (549 mg, 4 mmoles) and $NEt_3$ (1.0 g, 10 mmoles) followed by 2,2'-biphenol (370 mg, 2 mmoles) and $NEt_3$ (0.5 g, 5 mmoles). $^{31}P$ NMR ($C_6D_6$): 130.51 ppm.

EXAMPLE 5A

Hydrocyanation of 3-Pentenenitrile with Ligand "E"/Ni $(COD)_2$; $ZnCl_2$ promoter 285 mg of Ligand "E", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 60.6% ADN; 9.7% MGN, 1.5% ESN (selectivity to ADN: 84.4%)

EXAMPLE 6

Synthesis of the ligand of Formula III where each $R^1$ is ethyl and each $R^{2'}$ is hydrogen and each $R^4$ and $R^{4'}$ are methyl; each $R^2$ para to oxygen is methyl

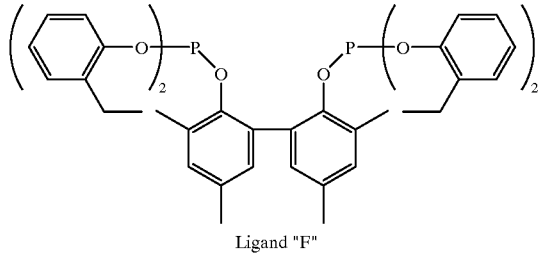

Ligand "F"

The procedure is the same as Example 1 but with 2-ethylphenol (978 mg, 8 mmoles), $PCl_3$ (550 mg, 4 mmoles) and $NEt_3$ (1.0 g, 10 mmoles) followed by 2,2'-ethylidenebis(4,6-dimethylphenol) (370 mg, 2 mmoles), prepared according to Yamada et al., *Bull Chem. Soc. Jpn.*, 1989, 62, 3603, and $NEt_3$ (0.4 g, 4 mmoles). $^{31}P$ NMR ($C_6D_6$): 134.91 ppm with minor peaks due to impurities at 136.24, 131.41, 131.18, 127.67, and 107.10ppm.

EXAMPLE 6A

Hydrocyanation of 3-Pentenenitrile with Ligand "F"/Ni $(COD)_2$; $ZnCl_2$ promoter 343 mg of Ligand "F", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 72.2% ADN; 9.7% MGN, 1.3% ESN (selectivity to ADN: 86.7%)

EXAMPLE 7

Synthesis of the ligand of Formula II where each $R^1$ is methyl, each $R^{2'}$ is hydrogen and $R^2$ is $CO_2Me$

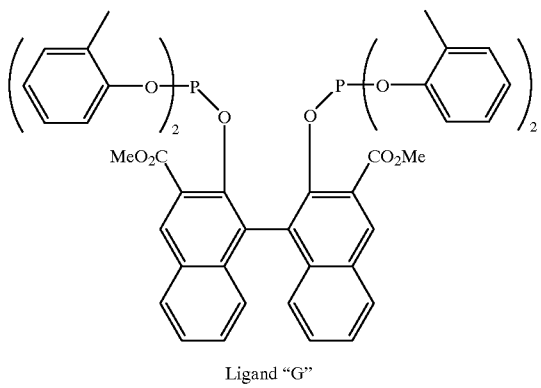

Ligand "G"

The procedure is the same as Example 1 but with o-cresol (866 mg, 8 mmoles), $PCl_3$ (550 mg, 4 mmoles) and $NEt_3$ (0.9 g, 9 mmoles) followed by dimethyl 2,2'-diydroxy-1,1'-binaphthalene-3,3'-dicarboxylate (804 mg, 2 mmoles), prepared according to the literature: *J Am. Chem. Soc.*, 1954, 76,296 and *Tetrahedron Lett.*, 1990, 413, and $NEt_3$ (0.6 g, 6 mmoles). $^{31}P$ NMR ($CD_2Cl_2$): 130.09 ppm with minor peaks due to impurities at 145.32, 131.65, and 131.39 ppm.

EXAMPLE 7A

Hydrocyanation of 3-Pentenenitrile with Ligand "G"/Ni $(COD)_2$; $ZnCl_2$ promoter To 5 mL of THF was added 40 mg of Ni(COD)$_2$, and 374 mg of ligand "G". The solvent was removed by vacuum evaporation and 5 mL of 3-pentenenitrile and 20 mg ZnCl$_2$ were added. The mixture was treated with HCN at a nitrogen flow rate of 30 mL/min at 70° C. for one hour. The mixture was analyzed by GC analyses indicates 51.7% ADN; 3.7% MGN; 0.4 ESN (selectivity to ADN: 92.6%)

EXAMPLE 8

Synthesis of the ligand of Formula I where each $R^1$ is methyl, each $R^{2'}$ is para to $R^1$ methyl, $R^2$ para to the oxygen is methyl, $R^2$ ortho to the oxygen is OMe and remaining $R^{2'}$ are hydrogen

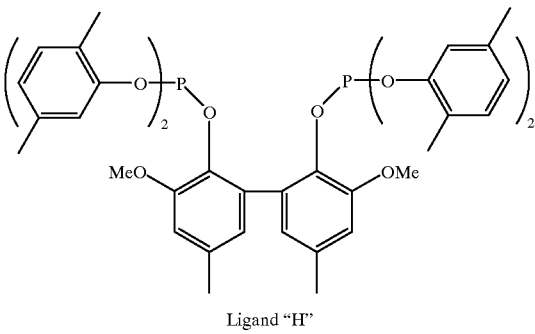

Ligand "H"

The procedure is the same as Example 1 but with 2,5-dimethylphenol (978 mg, 8 mmoles), $PCl_3$ (550 mg, 4 mmoles) and $NEt_3$ (1.0 g, 10 mmoles) followed by 2,2'-dihydroxy-3,3'-dimethoxy-5,5'-dimethyl-1,1'-biphenylene (550 mg, 2 mmoles), and $NEt_3$ (0.4 g, 4 mmoles). $^{31}P$ NMR ($C_6D_6$): 133.64 with minor peaks due to impurities at 144.82, 137.03, 134.52, 131.99 ppm.

EXAMPLE 8A

Hydrocyanation of 3-Pentenenitrile with Ligand "H"/Ni $(COD)_2$; $ZnCl_2$ promoter 352 mg of Ligand "H", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 58.0% ADN, 5.9% MGN, and 0.4% ESN (selectivity to ADN: 90.2%).

EXAMPLE 9

Synthesis of the ligand of Formula I where each $R^1$ is methyl, each $R^{2'}$ orthro is t-butyl, $R^2$ para to the oxygen is methyl, $R^{2'}$ ortho to the oxygen is OMe and remaining $R^{2'}$ are hydrogen

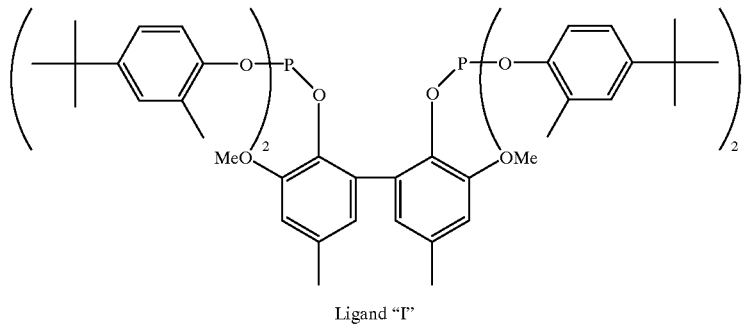

Ligand "I"

The procedure is the same as Example 1 but with 2-methyl-4-t-butylphenol (1.314 g, 8 mmoles), PCl$_3$ (550 mg, 4 mmoles) and NEt$_3$ (0.9 g, 9 mmoles) followed by 2,2'-dihydroxy-3,3'-dimethoxy-5,5'-dimethyl-1,1'-biphenylene (550 mg, 2 mmoles), and NEt$_3$ (0.6 g, 6 mmoles). $^{31}$P NMR (C$_6$D$_6$): 134.32 ppm with minor peaks due to impurities at 148.97, 145.04, 135.30, 134.99, 134.55, 134.46, 134.40, 132.00 ppm.

EXAMPLE 9A

Hydrocyanation of 3-Pentenenitrile with Ligand "I"/Ni (COD)$_2$; ZnCl$_2$ promoter 415 mg of Ligand "I", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 71.0% ADN, 6.7% MGN, and 0.8% ESN (selectivity to ADN: 90.2%).

EXAMPLE 10

Synthesis of the ligand of Formula I where each $R^1$ is methyl, $R^{2'}$ is hydrogen, $R^2$ para to the oxygen is CH$_2$CH=CH$_2$, $R^2$ ortho to the oxygen is OMe

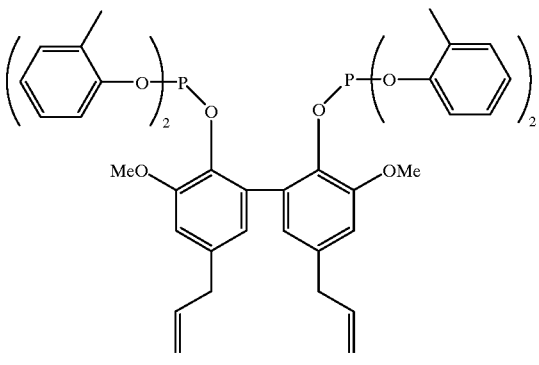

Ligand "J"

The procedure is the same as Example 1 but with o-cresol (865 mg, 8 moles), PCl$_3$ (550 mg, 4 mmoles) and NEt$_3$ (1.0 g, 10 mmoles) followed by dihydrodieugenol (653 mg, 2 mmoles), prepared according to *Phytochemistry*, 1988,27, 3008 and NEt$_3$ (0.4 g, 4 mmoles). $^{31}$P NMR (C$_6$D$_6$): 133.62 ppm with minor peaks due to impurities at 137.33, 134.20, and 131.41 ppm.

EXAMPLE 10A

Hydrocyanation of 3-Pentenenitrile-with Ligand "J"/Ni (COD)$_2$; ZnCl$_2$ promoter 355 mg of Ligand "J", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 78.1% ADN, 5.8% MGN, and 0.6% ESN (selectivity to ADN: 92.4%).

EXAMPLE 11

Synthesis of the Ligand of Formula II where each $R^1$ is methyl, $R^2$ is methyl, $R^{2'}$ hydrogen

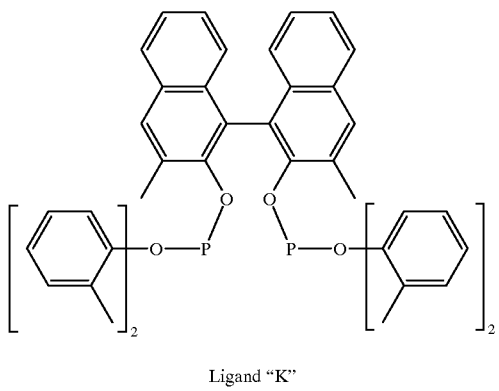

Ligand "K"

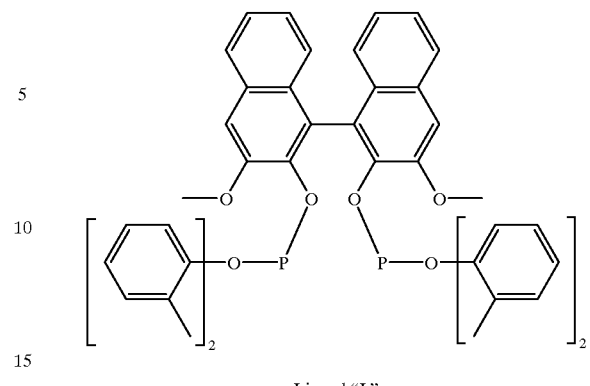

Ligand "L"

In the drybox, Et$_2$NPCl$_2$ (6.92 gm, 39.7 mmol) and triethylamine (10.1 gm, 100 mmol) were added to a 250 mL round bottom flask with a magnetic stirbar and 100 mL dry ether. This solution was cooled to −30° C. in the drybox freezer. Ortho-cresol was diluted in dry ether (50 mL) then poured dropwise into the stirred cold ether solution of PCl$_2$(NEt$_2$) and triethylamine. The reaction mixture was allowed to warm to ambient temperature with stirring. After two hours at ambient temperature, a $^{31}$P NMR analysis indicated that the reaction was complete (single signal at 142.2 ppm). The triethylammonium chloride salts were filtered from the ether solution then washed with dry ether (2×50 mL). The ether filtrates were evaporated to yield (2-CH$_3$C$_6$H$_4$O)$_2$PNEt$_2$ as an oil.

In the drybox, (2-CH$_3$C$_6$H$_4$O)$_2$PNEt$_2$ (1.59 gm, 5.0 mmol) was added to a 100 mL round bottom flask with a magnetic stirbar and 50 mL dry toluene. This solution was cooled to −30° C. in the drybox freezer then a 1.0 M hydrogen chloride solution in ether (10.0 niL, 10.0 mmol) was added dropwise with a syringe. An analysis of the resulting toluene/ether solution by $^{31}$P NMR indicated that (2-CH$_3$C$_6$H$_4$O)$_2$PNEt$_2$ had been completely converted to (2-CH$_3$C$_6$H$_4$O)$_2$PCl (δ=162 ppm). The diethylammonium chloride solids were separated from the toluene/ether solution by filtration then washed with dry toluene (2×5 mL). The ether was evaporated from the combined filtrates then 3,3'-dimethyl-2,2'-dihydroxy-1,1'-binaphthalene (0.63 gm, 2.0 mmol) was added followed by dry triethylamine (0.61 gm, 6.0 mmol). The mixture was stirred at ambient temperature overnight. A $^{31}$P NMR analysis of the resulting solution showed a signal for the major phosphite product at 132 ppm with minor signals at 143, 134, 131, and 127 ppm.

EXAMPLE 11A

Hydrocyanation of 3-Pentenenitrile with Ligand "K"/Ni (COD)$_2$; ZnCl$_2$ promoter 338 mg of Ligand "K", 40 mg Ni(COD)$_2$, and 20 mg of ZnCl$_2$ were dissolved in 5 mL of 3-penteneaitrile. The mixture was treated with HCN at a nitrogen flow rate of 30 mL/min at 70° C. for one hour. GC analysis indicated 85.0% ADN, 6.0% MGN, and 1.3% ESN (selectivity to ADN: 92.1%).

EXAMPLE 12

Synthesis of the Ligand of Formula II where each R$^1$ is methyl, each R$^2$ is methoxy, and each R$^{2'}$ is hydrogen 3,3'-Dimethoxy-2,2'-dihydroxy-1,1'-binaphthalene was prepared by oxidatively coupling 3-methoxy-2-naphthol (Recl. Trav. Chim. Pays. Bas. 1995, 112, 216) in toluene with oxygen and Cu(TMEDA)(OH)Cl catalyst (TMEDA= tetramethylethylenedimine) as described in Tetrahedron Lett. 1990, 413.

A toluene solution of (2-CH$_3$C$_6$H$_4$O)$_2$PCl (5 mmol) was prepared as described in Example 11. This phosphorochloridite was reacted with 3,3'-dimethoxy-2,2'-dihydroxy-1,1'-binaphthalene (0.693 gm, 2.0 mmol) in the presence of excess triethylamine base using the procedure described in Example 11. A $^{31}$P NMR analysis gave a major phosphite signal at 130.8 ppm with minor signals at 146 and 131.4 ppm.

EXAMPLE 12A

Hydrocyanation of 3-Pentenenitrile with Ligand "L"/Ni (COD)$_2$; ZnCl$_2$ promoter 351 mg of Ligand "L", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 71.7% ADN, 5.4% MGN, and 0.6% ESN (selectivity to ADN: 92.2%).

EXAMPLE 13

Synthesis of the Ligand of Formula II where each R$^2$ is phenyl carboxylate, each R$^1$ is methyl, and each R$^{2'}$ is hydrogen

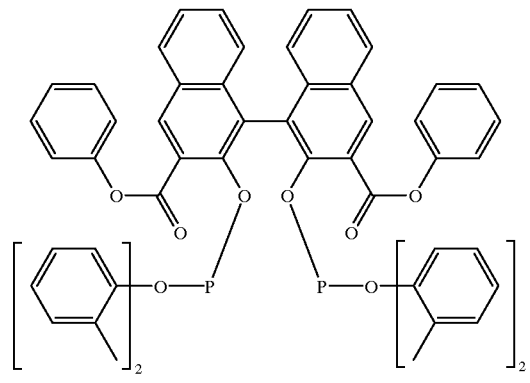

Ligand "M"

Diphenyl 2,2'-dihydroxy-1,1'-binaphthalene-3,3'-dicarboxylate was prepared by oxidatively coupling phenyl 2-hydroxy-3-naphthoate in toluene with oxygen and Cu(TMEDA)(OH)Cl catalyst as described in *Tetrahedron Lett.* 1990, 413.

A toluene solution of $(2\text{-}CH_3C_6H_4O)_2PCl$ (5 mmol) was prepared as described in Example 11. This phosphorochloridite was treated with diphenyl 2,2'-dihydroxy-1,1'-binaphthalene-3,3'-dicarboxylate (1.05 gin, 2.0 mmol) in the presence of excess triethylamine base using the procedure described in Example 11. A $^{31}$P NMR analysis gave a major phosphite signal at 130 ppm with minor signals at 131 and 127 ppm.

EXAMPLE 13A
Hydrocyanation of 3-Pentenenitrile with Ligand "M"/Ni $(COD)_2$; $ZnCl_2$ promoter 426 mg of Ligand "M", 40 mg $Ni(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 13.6% ADN, 1.0% MGN, and 0.1% ESN (selectivity to ADN: 92.6%).

EXAMPLE 14
Synthesis of the Ligand of Formula II where each $R^2$ is isopropyl carboxylate, each $R^1$ is methyl, and each $R^{2'}$ is hydrogen

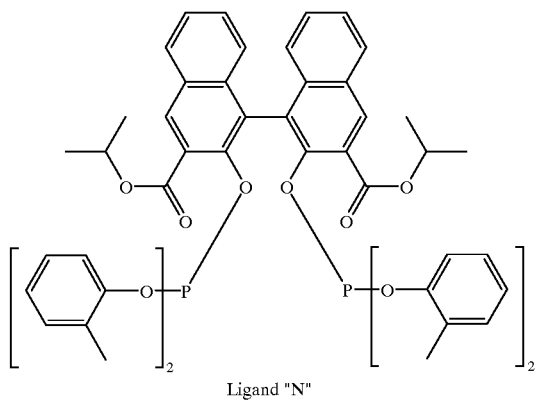

Ligand "N"

Diisopropyl 2,2'-dihydroxy-1,1'-binaphthalene-3,3'-dicarboxylate was prepared by oxidatively coupling isopropyl 2-hydroxy-3-naphthoate in toluene with oxygen and Cu(TMEDA)(OH)Cl catalyst as described in *Tetrahedron Lett.* 1990, 413.

A toluene solution of $(2\text{-}CH_3C_6H_4O)_2PCl$ (5 mmol) was prepared as described in Example 11. This phosphorochloridite was treated with diisopropyl 2,2'-dihydroxy-1,1'-binaphthalene-3,3'-dicarboxylate (0.917 gm, 2.0 mmol) in the presence of excess triethylamine base using the procedure described in Example 11. A $^{31}$P NMR analysis gave a major phosphite signal at 129.9 ppm with minor signals at 131.3, 131.2 and 127 ppm.

EXAMPLE 14A
Hydrocyanation of 3-Pentenenitrile with Ligand "N"/Ni $(COD)_2$; $ZnCl_2$ promoter 398 mg of Ligand "N", 40 mg $Ni(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 52.3% ADN, 3.2% MGN, and 0.4% ESN (selectivity to ADN: 93.5%).

EXAMPLE 15
Synthesis of the Ligand of Formula I where each $R^1$ is methyl, each $R^{2'}$ is hydrogen, and each $R^2$ ortho and para to oxygen is methyl

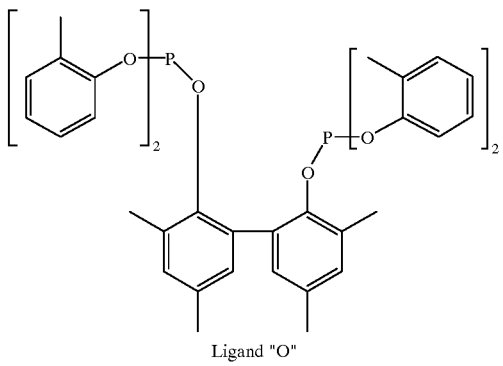

Ligand "O"

To a 200 mL round bottom flask, 0.86 g o-cresol (8 mmol) and 0.55 g $PCl_3$ (4 mmol) were added, followed by the addition of 100 mL dry toluene. The flask was cooled to −20° C. and a precooled toluene solution (−20° C., 20 mL) containing 1.0 g $NEt_3$ (10 mmol) was added dropwise. A toluene solution (20 mL) containing 0.48 g 3,3',5,5'-tetramethyl-2,2'-biphenol (2 mmol, prepared using a literature procedure: W. W. Kaeding, *J. Org. Chem.*, 1963, 28, 1063 and 0.6 g $NEt_3$ (6 mmol) was added to the above solution and stirred overnight. The mixture was filtered, washed with 10 mL toluene and the solvent was evaporated under vacuum. After drying under vacuum for one day, a yellow oil was obtained (1.4 g). A $^{31}$P NMR analysis gave a major signal at 133.8 ppm with minor signals at 142.2 and 131.5. APCI (atmospheric pressure chemical ionization) MS (m/z): Found: 731.63 ($M^+$−H); calculated for $M^+$−H $(C_{44}H_{46}O_6P_2\text{−H})$: 731.27.

EXAMPLE 15A
Hydrocyanation of 3-Pentenenitrile with Ligand "O"/Ni $(COD)_2$ with Zinc Chloride Promoter 308 mg of Ligand "O", 40 mg $Ni(COD)_2$, and 20 mg of $ZnCl_2$ were dissolved in 5 mL of 3-pentenenitrile. The mixture was treated with HCN at a nitrogen flow rate of 30 mL/min at 70° C. for one hour. GC analysis indicated 69.1% ADN, 3.7% MGN, and 0.7% ESN (selectivity to ADN: 94%).

EXAMPLE 16
Synthesis of the Ligand of Formula I where each $R^1$ is methyl, each $R^{2'}$ is hydrogen, each $R^2$ ortho and meta to oxygen is methyl

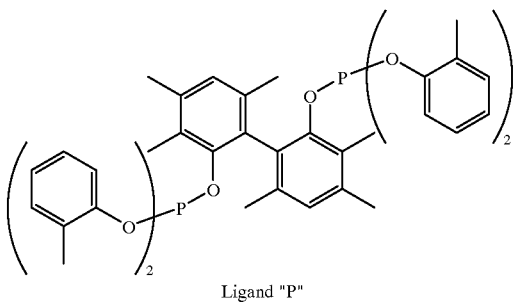

Ligand "P"

This ligand was prepared similar to Ligand "O" but 3,3',4,4',6,6'-hexamethyl-2,2'-biphenol (prepared by coupling of 2,3,5-trimethylphenol using the literature procedure for 3,3',5,5' tetramethyl-2,2'-biphenol: W. W. Kaeding, *J. Org. Chem.*, 1963, 28, 1063 was used as the backbone. $^{31}$P NMR (C$_6$D$_6$): 13 5.2 ppm. APCI MS (m/z): Found: 759.72 (M$^+$+H); calculated for M$^+$+H (C$_{46}$H$_{48}$O$_6$P$_2$+H): 759.30.

EXAMPLE 16A

Hydrocyanation of 3-Pentenenitrile with Ligand "P"/Ni (COD)$_2$ with Zinc Chloride Promoter 318 mg of Ligand "P", 40 mg Ni(COD)$_2$, and 20 mg of ZnCl$_2$ were dissolved in 5 mL of 3-Pentenenitrile. The mixture was treated with HCN at a nitrogen flow rate of 30 mL/min at 70° C. for one hour. GC analysis indicated 90.4% ADN, 3.9% MGN, and 0.5% ESN (selectivity to ADN: 95%).

EXAMPLE 17

Synthesis of the Ligand of Formula I where each R$^1$ and R$^{2'}$ adjacent to R$^1$ is the linking group -(CH$_2$)$_4$-, remaining R$^{2'}$ are hydrogen, each R$^2$ ortho and para to oxygen is methyl

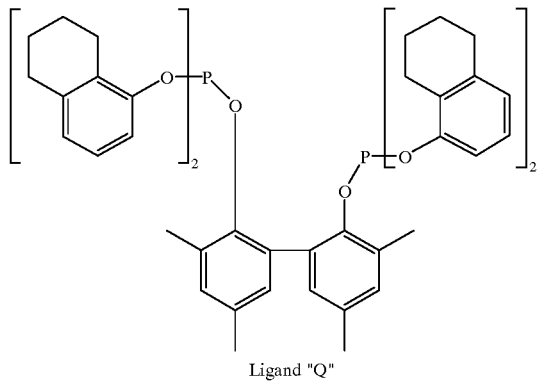

Ligand "Q"

To a 200 mL round bottom flask, 1.18 g 1,2,3,4-tetrahydro-1-naphthol (8 mmol) and 0.55 g PCl$_3$ (4 mmol) were added, followed by the addition of 100 mL dry toluene. The flask was cooled to −20° C. and a precooled toluene solution (−20° C., 20 mL) containing 1.0 g NEt$_3$ (10 mmol) was added dropwise. About 1 hour later, a toluene solution (20 mL) containing 0.48 g 3,3',5,5'-tetramethyl-2,2'-biphenol (2 mmol) and 0.6 g NEt$_3$ (6 mmol) was added to the above solution and stirred overnight. The mixture was filtered, washed with 10 mL toluene and the solvent was taken off under vacuum. After drying under vacuum for one day, a yellow oil was obtained (1.8 g, toluene present in the $^1$H NMR spectrum). $^{31}$P NMR (C$_6$D$_6$) indicated a major signal at 134.1 ppm with minor signals at 142.2 and 131.4 ppm. APCI MS (m/z): Found: 891.21 (M$^+$−H); calculated for M$^+$−H (C$_{56}$H$_{62}$O$_6$P$_2$−H): 891.39.

EXAMPLE 17A

Hydrocyanation of 3-Pentenenitrile with Ligand "Q"/Ni (COD)$_2$ with Zinc Chloride Promoter 375 mg of Ligand "Q", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 85.6% ADN, 4.8% MGN, and 1.4% ESN (selectivity to ADN: 93%).

EXAMPLE 18

Synthesis of the Ligand of Formula I where each R$^1$ and R$^{2'}$ adjacent to R$^1$ is the linking group -(CH$_2$)$_4$-, remaining R$^{2'}$ are hydrogen, each R$^2$ ortho to oxygen is methoxy and each R$^2$ para to oxygen is methyl

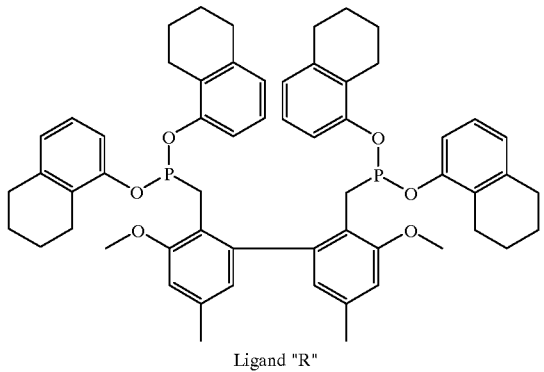

Ligand "R"

This ligand was prepared similar to Ligand "Q" but 3,3'-dimethoxy-5,5'-dimethyl-2,2'-dihydroxy-1,1'-biphenylene [prepared by coupling 2-methoxy4-methylphenol using the procedure described in *Phytochemistry* 1988, 27, 3008] was used instead of 3,3',5,5'-tetramethyl-2,2'-biphenol as the backbone. After the usual workup, the residue was vacuum dried and then treated with 100 mL of isopropyl alcohol. A solid formed which was collected and vacuum dried to give the desired product as a white solid. $^{31}$P NMR (C$_6$D$_6$): 134.6 ppm with minor peak due to an impurity at 145.6 ppm.

EXAMPLE 18A

Hydrocyanation of 3-Pentenenitrile with Ligand "R"/Ni (COD)$_2$ with Zinc Chloride Promoter 388 mg of Ligand "R", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 80.2% ADN, 6.1% MGN, and 0.7% ESN (selectivity to ADN: 92%).

EXAMPLE 19

Synthesis of the Ligand of Formula III where each R$^1$ and R$^{2'}$ adjacent to R$^1$ is the linking group -(CH$_2$)$_4$-, remaining R$^{2'}$ are hydrogen, each R$^4$ and R$^{4'}$ is methyl, each R$^2$ para to oxygen is methyl and the remaining R$^2$ are hydrogen

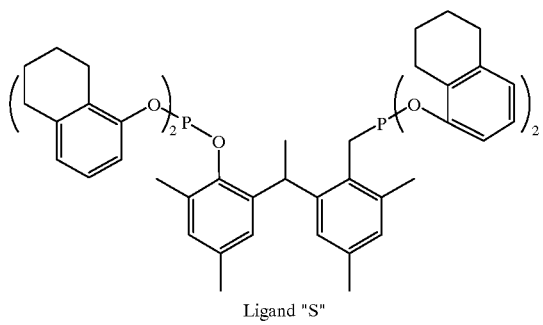

Ligand "S"

This ligand was prepared similar to Ligand "Q" but 2,2'-ethylidenebis(4,6-dimethylphenol) [prepared according to Yamada et al., *Bull. Chem. Soc. Jpn.* 1989, 62, 3603] was used instead of 3,3',5,5'-tetramethyl-2,2'-biphenol as the backbone. $^{31}$P NMR (C$_6$D$_6$): 134.5 ppm with a minor peak due to an impurity at 131.5 ppm.

EXAMPLE 19A
Hydrocyanation of 3-Pentenenitrile with Ligand "S"/Ni (COD)$_2$ with Zinc Chloride Promoter 390 mg of Ligand "S", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 71.1% ADN, 11.5% MGN, and 1.3% ESN (selectivity to ADN: 85%).

EXAMPLE 20
Synthesis of the Ligand of Formula IV where each $R^1$ and $R^{2'}$ meta to $R^1$ are methyl, remaining $R^{2'}$ are hydrogen, each $R^2$ ortho and para to oxygen is methyl

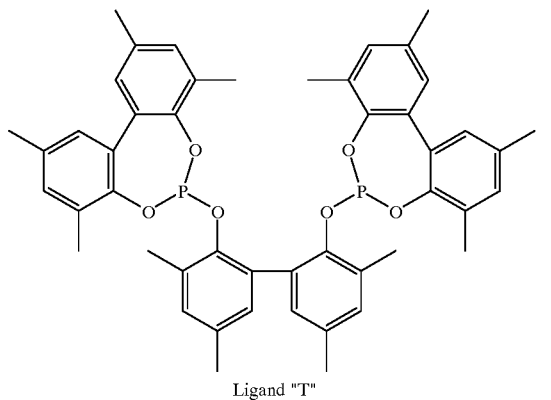

Ligand "T"

To a 300 mL round bottom flask, 1.92 g 3,3',5,5'-tetramethyl-2,2-biphenol (8 mmol) and 1.10 g PCl$_3$ (8 mmol) were added, followed by the addition of 200 mL dry toluene. The flask was cooled to −20° C. and a precooled toluene solution (−20° C., 20 mL) containing 2.0 g NEt$_3$ (20 mmol) was added dropwise. A toluene solution (20 mL) containing 0.96 g 3,3',5,5'-tetramethyl-2,2'-biphenol (4 mmol) and 1.2 g NEt$_3$ (12 mmol) was added to the above solution and stirred overnight. The usual workup gave 3.0 g of white solid. $^{31}$P NMR: 144.6 ppm. APCI MS (m/z): Found: 782.96 (M$^+$+H); calculated for M$^+$+H (C$_{48}$H$_{48}$O$_6$P$_2$+H): 783.30.

EXAMPLE 20A
Hydrocyanation of 3-Pentenenitrile with Ligand "T"/Ni (COD)$_2$ with Zinc Chloride Promoter 329 mg of Ligand "T", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 41.1% ADN, 8.8% MGN, and 0.8% ESN (selectivity to ADN: 81%).

EXAMPLE 21
Synthesis of the Ligand of Formula V where each $R^1$ and $R^{2'}$ meta to $R^1$ is methyl, each $R^2$ is hydrogen

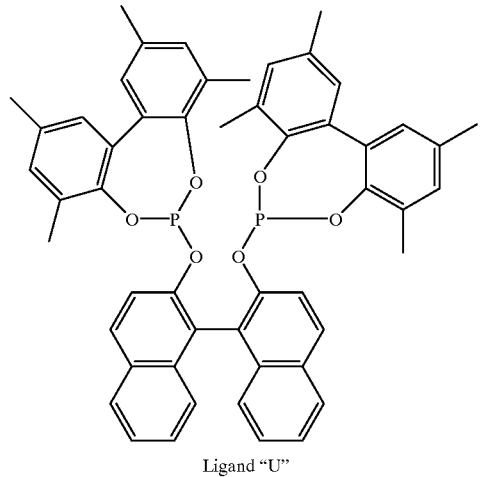

Ligand "U"

This ligand was prepared similar to Ligand "T" but 1,1'-bi-2-naphthol was used instead of 3,3',5,5'-tetramethyl-2,2'-biphenol as the backbone. $^{31}$P NMR (C$_6$D$_6$): 142.2 ppm. APCI MS (m/z): Found: 826.94 (M$^+$+H); calculated for M$^+$+H (C$_{52}$H$_{44}$O$_6$P$_2$+H): 827.27.

EXAMPLE 21A

Hydrocyanation of 3-Pentenenitrile with Ligand "U"/Ni (COD)$_2$ with Zinc Chloride Promoter 347 mg of Ligand "U", 40 mg Ni(COD)$_2$, and 20 mg of ZnCl$_2$ were dissolved in 5 mL of 3-pentenenitile. The mixture was treated with HCN at a nitrogen flow rate of 30 mL/min at 70° C. for one hour. GC analysis indicated 68.2% ADN, 22.3% MGN, and 3.0% ESN (selectivity to ADN: 73%).

EXAMPLE 22

Synthesis of the Ligand of Formula VI where each $R^1$ and $R^{2'}$ meta to $R^1$ is methyl, each $R^4$ is methyl, each $R^2$ para to oxygen is methyl

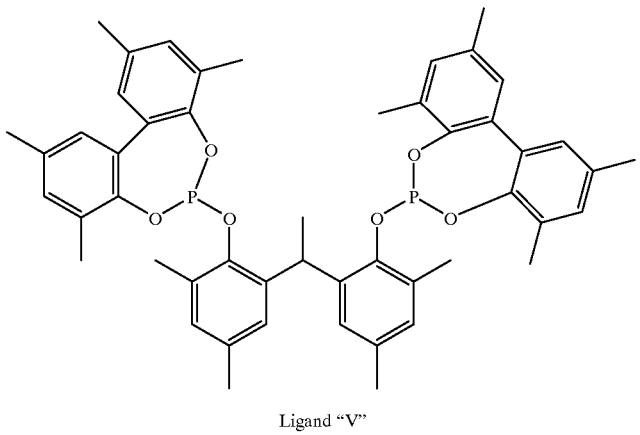

Ligand "V"

This ligand was prepared similar to Ligand "T" but 2,2'-ethylidenebis(4,6-dimethylphenol) (prepared using a literature procedure: F. Yamada, T. Nishiyama, M. Yamamoto, K. Tanaka, *Bull. Chem Soc. Jpn.,* 1989, 62, 3603 was used instead of 3,3',5,5'-tetramethyl-2,2'-biphenol as the backbone. $^{31}$P NMR ($C_6D_6$): 144.6 ppm as the major signal with minor signal at 135.1 ppm. FAB MS (m/z): Found: 811.45 ($M^+$+H); calculated for $M^+$+H ($C_{50}H_{52}O_6P_2$+H): 811.33.

EXAMPLE 22A
Hydrocyanation of 3-Pentenenitrile with Ligand "V"/Ni (COD)$_2$ with Zinc Chloride Promoter 340 mg of Ligand "V", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 66.3% ADN, 22.7% MGN, and 2.2% ESN (selectivity to ADN: 73%).

EXAMPLE 23
Synthesis of the Ligand of Formula IX where each $R^1$ is methyl, $R^{4'}$ in the methylene bridge is hydrogen, each $R^4$ ortho to the oxygen is methyl, $R^2$ is hydrogen

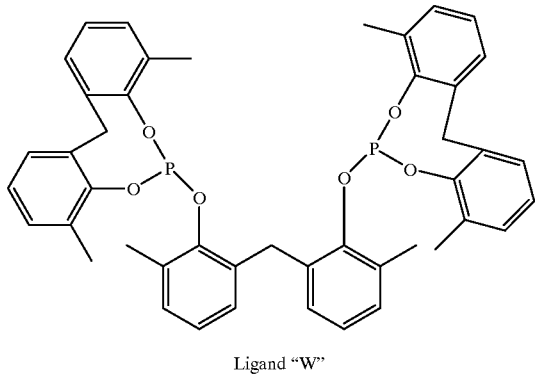

Ligand "W"

In a flask were added 0.92 g 3,3'-dimethyl-2,2'-dihydroxydiphenylmethane (4 mmol, prepared by a literature procedure: G. Casiraghi, G. Casnati, A. Pochini, G. Puglia, R Ungaro, G. Sartori, *Synthesis,* 1981, 2, 143, 0.55 g PCl$_3$ (4 mmol) and 100 mL of dry toluene. The flask was cooled to –20° C. and a precooled toluene solution (–20° C., 20 mL) containing 1.0 g NEt$_3$ (10 mmol) was added dropwise. A toluene solution (20 mL) containing 0.46 g (2 mmol) 3,3'-dimethyl-2,2'-dihydroxydiphenylmethane and 0.6 g NEt$_3$ (6 mmol) was added to the above solution and stirred overnight. The mixture was filtered, washed with 10 mL toluene and the solvent was evaporated under vacuum. After drying under vacuum for one day, a white solid was obtained (1.5 g, toluene detected in the $^1$H NMR spectrum). $^{31}$P NMR ($C_6D_6$): 138.2 ppm.

EXAMPLE 23A
Hydrocyanation of 3-Pentenenitrile with Ligand "W"/Ni (COD)$_2$ with Zinc Chloride Promoter 311 mg of Ligand "W", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 47.2% ADN, 14.7% MGN, and 2.5% ESN (selectivity to ADN: 73%).

EXAMPLE 24
Synthesis of the Ligand of Formula VII where each $R^1$ is methyl, each $R^{2'}$ is hydrogen, each $R^2$ are hydrogen

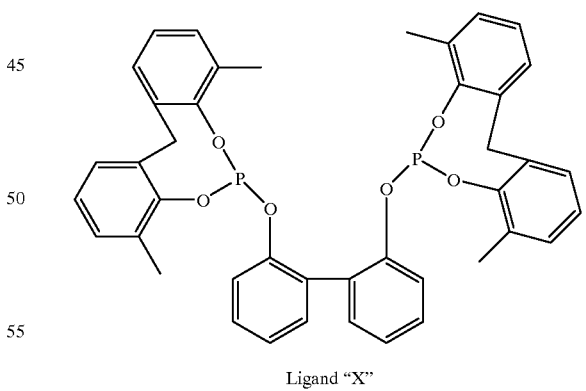

Ligand "X"

This ligand was prepared similar to Ligand "W" but 2,2'-biphenol was used instead of 3,3'-dimethyl-2,2'-dihydroxydiphenylmethane as the backbone. $^{31}$P NMR ($C_6D_6$): 128.1 ppm. APCI MS (m/z): Found: 699.85 ($M^+$+H); calculated for $M^+$+H ($C_{42}H_{36}O_6P_2$+H): 699.20.

EXAMPLE 24A
Hydrocyanation of 3-Pentenenitrile with Ligand "X"/Ni (COD)$_2$ with Zinc Chloride Promoter 293 mg of Ligand "X", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 55.3% ADN, 10.6% MGN, and 1.8% ESN (selectivity to ADN: 82%).

EXAMPLE 25

Synthesis of the Ligand of Formula VIII where each $R^1$ is methyl, each $R^2$ is hydrogen, each $R^{2'}$ is hydrogen

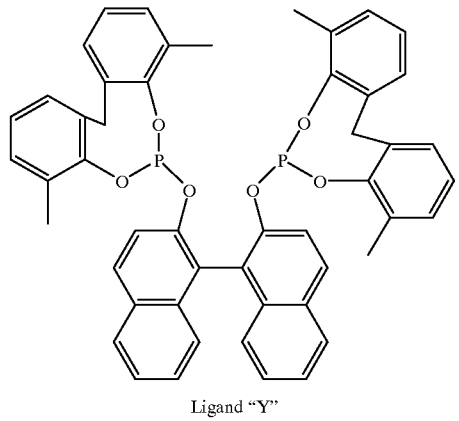

Ligand "Y"

This ligand was prepared similar to Ligand "T" but 1,1'-bi-2-naphthol was used instead of 3,3'-dimethyl-2,2'-dihydroxydiphenylmethane as the backbone. $^{31}$P NMR (C$_6$D$_6$): 129.8 ppm. APCI MS (m/z): Found: 799.21 (M$^+$+H); calculated for M$^+$+H (C$_{50}$H$_{40}$O$_6$P$_2$+H): 799.23.

EXAMPLE 25A

Hydrocyanation of 3-Pentenenitrile with Ligand "Y"/Ni (COD)$_2$ with Zinc Chloride Promoter 335 mg of Ligand "Y", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 74.4% ADN, 14.8% MGN, and 3.6% ESN (selectivity to ADN: 80%).

EXAMPLE 26

Synthesis of the Ligand of Formula VII where each $R^1$ and $R^{2'}$ para to $R^1$ is methyl, remaining $R^{2'}$ are hydrogen, each $R^2$ is hydrogen

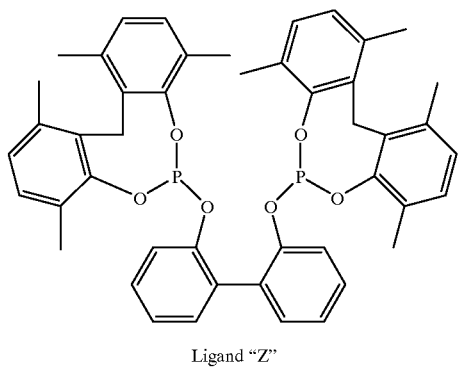

Ligand "Z"

To a flask were added 1.02 g 3,3',6,6'-tetramethyl-2,2'-dihydroxydi-phenylmethane (4 mmol), 0.55 g PCl$_3$ (4 mmol) and 100 mL of dry toluene. The flask was cooled to −20° C. and a precooled toluene solution (−20° C., 20 mL) containing 1.0 g NEt$_3$ (10 mmol) was added dropwise. A toluene solution (20 mL) containing 0.37 g 2,2'-biphenol (2 mmol) and 0.6 g NEt$_3$ (6 mmol) was added to the above solution and stirred overnight. The mixture was filtered, washed with 10 mL toluene and the solvent was taken off under vacuum. After drying under vacuum for one day, a yellow solid was obtained (1.6 g). $^{31}$P NMR (CDCl$_3$): 130.2 ppm. APCI MS (m/z): Found: 755.11 (M$^+$+H); calculated for M$^+$+H (C$_{46}$H$_{44}$O$_6$P$_2$+H): 755.27.

EXAMPLE 26A

Hydrocyanation of 3-Pentenenitrile with Ligand "Z"/Ni (COD)$_2$ with Zinc Chloride Promoter 317 mg of Ligand "Z", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 85.3% ADN, 6.6% MGN, and 1.3% ESN (selectivity to ADN: 91%).

EXAMPLE 27

Synthesis of the Ligand of Formula IX where each $R^1$ and $R^{2'}$ para to $R^1$ is methyl, remaining $R^{2'}$ are hydrogen, each $R^4$ is methyl, $R^{4'}$ is hydrogen, $R^2$ para to oxygen is methyl, remaining $R^2$ are hydrogen

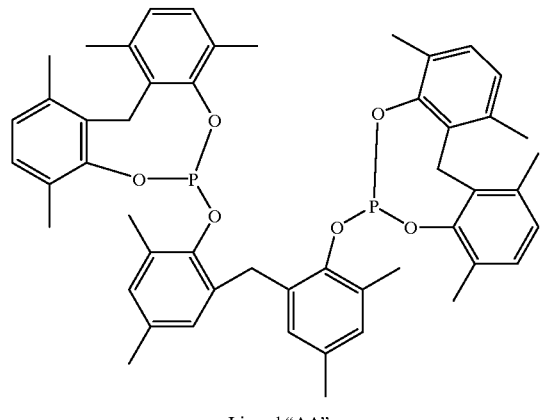

Ligand "AA"

This ligand was prepared similarly to Ligand "Z" except 3,3',5,5'-tetramethyl-2,2'-dihydroxydiphenylmethane was used instead of 2,2'-biphenol as the backbone. $^{31}$P NMR (CDCl$_3$): 131.36 ppm. APCI MS (m/z): Found: 825.22 (M$^+$+H); calculated for M$^+$+H (C$_{51}$H$_{54}$O$_6$P$_2$+H): 825.34.

EXAMPLE 27A

Hydrocyanation of 3-Pentenenitrile with Ligand "AA"/Ni (COD)$_2$ with Zinc Chloride Promoter 346 mg of Ligand "AA", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 49.2% ADN, 17.4% MGN, and 9.3% ESN (selectivity to ADN: 65%).

EXAMPLE 28

Synthesis of the Ligand of Formula VIII where each $R^1$ and $R^{2'}$ para to $R^1$ is methyl, remaining $R^{2'}$ are hydrogen, $R^2$ is hydrogen Ligand "AB"

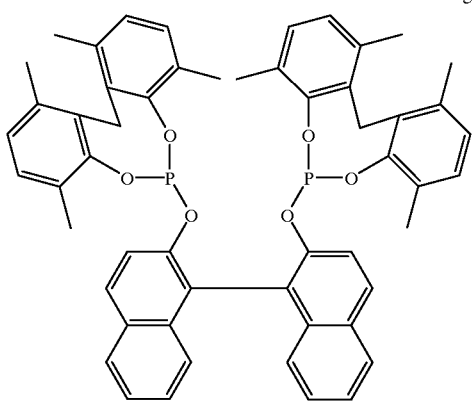

This ligand was prepared similar to Ligand "Z" except 1,1'-binaphthol was used instead of 2,2'-biphenol as the backbone. $^{31}$P NMR (C$_6$D$_6$): 130.73 ppm. APCI MS (m/z): Found: 855.60 (M$^+$+H); calculated for M$^+$+H (C$_{54}$H$_{48}$O$_6$P$_2$+H): 855.30.

EXAMPLE 28A
Hydrocyanation of 3-Pentenenitrile with Ligand "AB"/Ni(COD)$_2$ with Zinc Chloride Promoter 359 mg of Ligand "AB", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 84.2% ADN, 7.9% MGN, and 1.5% ESN (selectivity to ADN: 90%).

EXAMPLE 29
Synthesis of the Ligand of Formula VII where each R$^1$ and R$^{2'}$ para to R$^1$ is methyl, remaining R$^{2'}$ are hydrogen, each R$^2$ ortho to oxygen is methoxy, each R$^2$ para to oxygen is methyl, remaining R$^2$ are hydrogen Ligand "AC"

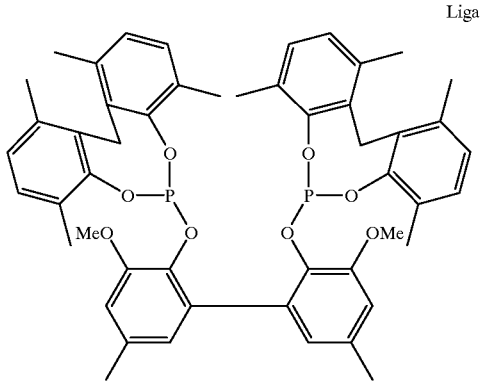

This ligand was prepared similar to Ligand "Z" except 3,3'-dimethoxy-5,5'-dimethyl-2,2'-biphenol was used instead of 2,2'-biphenol as the backbone. $^{31}$P NMR (C$_6$D$_6$): 133.28 ppm with a minor signal at 148.80 ppm due to an impurity. APCI MS (m/z): Found: 842.96 (M$^+$+H); calculated for M$^+$+H (C$_{50}$H$_{52}$O$_8$P$_2$+H): 843.32.

EXAMPLE 29A
Hydrocyanation of 3-Pentenenitrile with Ligand "AC"/Ni(COD)$_2$ with Zinc Chloride Promoter 354 mg of Ligand "AC", 40 mg Ni(COD)$_2$, and 20 mg of ZnCl$_2$ were dissolved in 5 mL of 3-pentenenitrile. The mixture was treated with HCN at a nitrogen flow rate of 30 mL/min at 70° C. for one hour. GC analysis indicated 53.1% ADN, 1.7% MGN, and 0.2% ESN (selectivity to ADN: 97%).

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A multidentate phosphite ligand selected from the group represented by the following Formula I, II, III, IV, V, VI, VII, VIII and IX:

Formula I

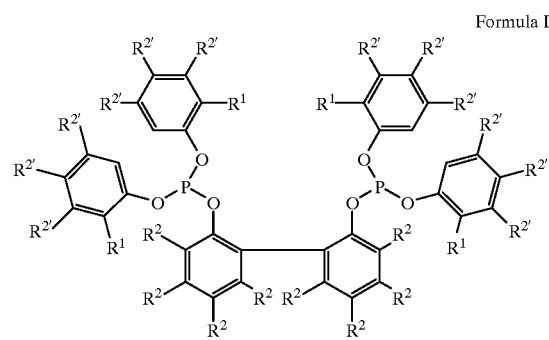

Formula II

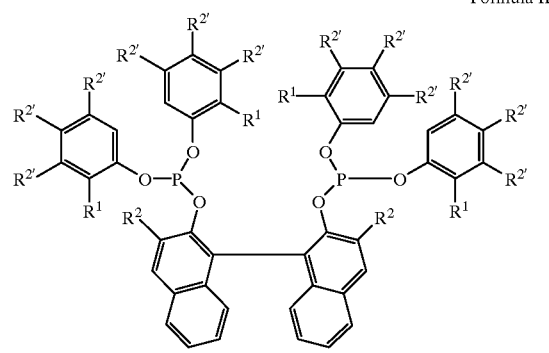

Formula III

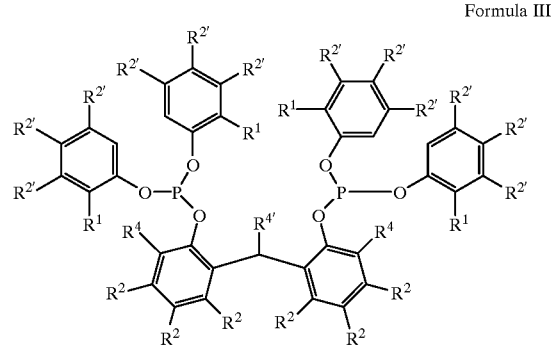

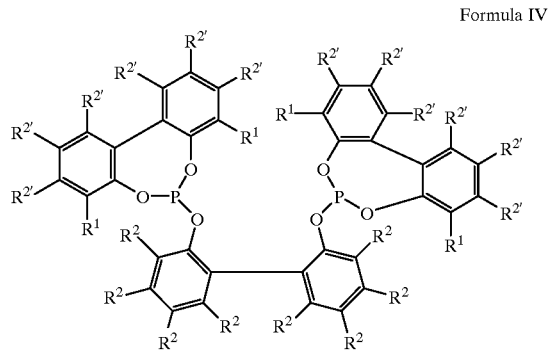

Formula IV

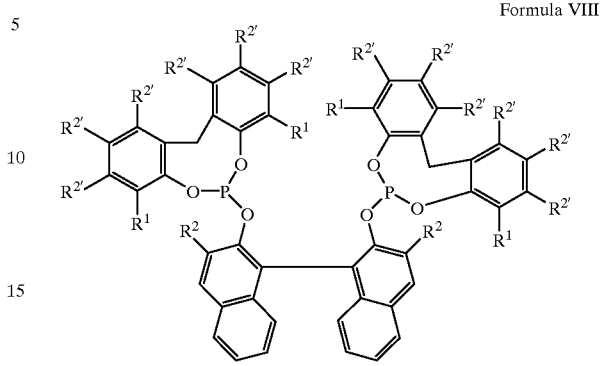

Formula VIII

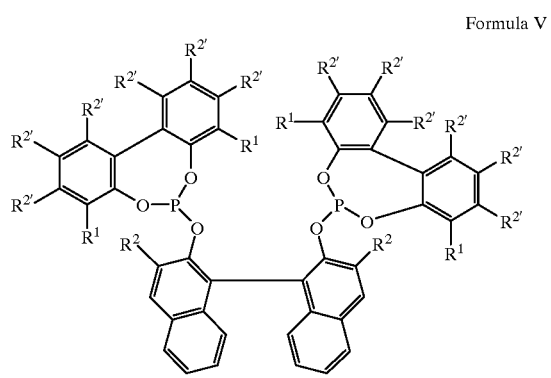

Formula V

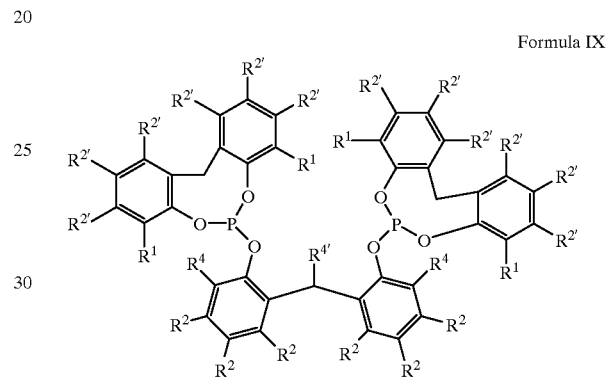

Formula IX

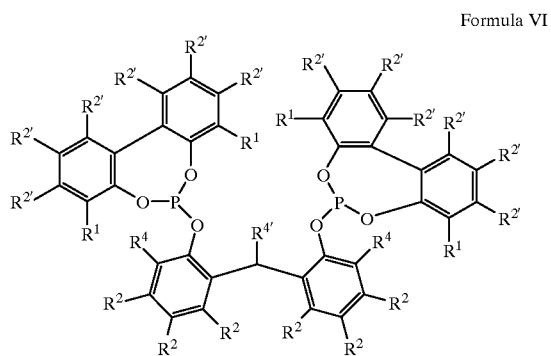

Formula VI

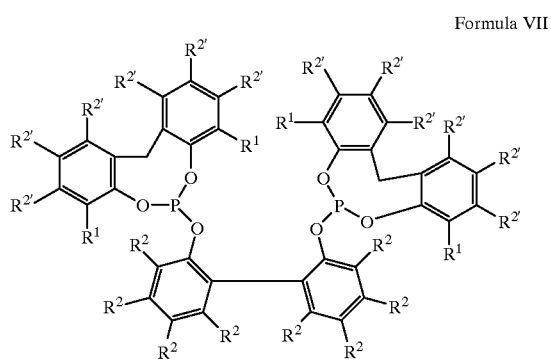

Formula VII wherein each $R^1$ is independently a primary, secondary, or tertiary hydrocarbyl of 1 to 12 carbon atoms; with the proviso that at least one of $R^1$ must be a primary hydrocarbyl;

each $R^2$ is independently H, halogen, primary or secondary hydrocarbyl of 1 to 12 carbon atoms, $OR^3$ wherein $R^3$ is a $C_1$ to $C_{12}$ alkyl, or $CO_2R^{3'}$ wherein $R^{3'}$ is an aryl or a $C_1$ to $C_{12}$ alkyl;

each $R^{2'}$ is independently H, halogen, CHO, primary, secondary or tertiary hydrocarbyl of 1 to 12 carbon atoms, $OR^3$ wherein $R^3$ is a $C_1$ to $C_{12}$ alkyl, $CO_2R^{3'}$ wherein $R^{3'}$ is an aryl or a $C_1$ to $C_{12}$ alkyl, or $C(R^3)(O)$ wherein $R^3$ is a $C_1$ to $C_{12}$ alkyl;

each $R^4$ is independently H, a primary or secondary hydrocarbyl of 1 to 12 carbon atoms or $CO_2R^3$ wherein $R^3$ is a $C_1$ to $C_{12}$ alkyl; and each $R^{4'}$ is independently H, a primary or secondary hydrocarbyl of 1 to 12 carbon atoms or aryl.

2. A catalyst precursor composition comprising zero-valent nickel and a multidentate phosphite ligand according to claim 1.

3. The catalyst precursor composition of claim 2 wherein a Lewis acid is also present.

4. The catalyst composition of claim 3 wherein the Lewis acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(tetrahydrofuran)_2$, $FeCl_2$, $TiCl_4$ (tetrahydrofuran)$_2$, TiCl$_4$, TiCl$_3$, ClTi(OiPr)$_3$, MnCl$_2$, ScCl$_3$, AlCl$_3$, (C$_8$H$_{17}$)AlCl$_2$, (C$_8$H$_{17}$)$_2$AlCl, (iso-C$_4$H$_9$)$_2$AlCl, (phenyl)$_2$AlCl, phenylAlCl$_2$, ReCl$_5$, ZrCl$_4$, NbCl$_5$, VCl$_3$, CrCl$_2$, MoCl$_5$, YCl$_3$, CdCl$_2$, LaCl$_3$, Er(O$_3$SCF$_3$)$_3$, Yb(O$_2$CCF$_3$)$_3$, SmCl$_3$, TaCl$_5$, CdCl$_2$, B(C$_6$H$_5$)$_3$, and (C$_6$H$_5$)$_3$SnX, where X=CF$_3$SO$_3$, CH$_3$C$_6$H$_5$SO$_3$, or (C$_6$H$_5$)$_3$BCN.

5. The catalyst precursor composition of claim 2 wherein the zero-valent nickel and the multidentate phosphite ligand are supported on the same solid support.

\* \* \* \* \*

UNITED STATES PATENT AND TRADEMARK OFFICE
CERTIFICATE OF CORRECTION

PATENT NO. : 6,171,996 B1  Page 1 of 1
DATED : January 9, 2001
INVENTOR(S) : James Michael Garner et al.

It is certified that error appears in the above-identified patent and that said Letters Patent is hereby corrected as shown below:

Column 18,
Line 29, after 1063, please insert -- ) -- thereof.

Column 19,
Line 3, after 1063, please insert -- ) -- thereof.

Column 23,
Line 24, after 3063, please insert -- ) -- thereof.

Signed and Sealed this

Twenty-fifth Day of December, 2001

Attest:

Attesting Officer

JAMES E. ROGAN
*Director of the United States Patent and Trademark Office*